(12) United States Patent
Yen et al.

(10) Patent No.: US 9,119,534 B2
(45) Date of Patent: Sep. 1, 2015

(54) OPTICAL APPARATUS AND OPERATING METHOD THEREOF

(75) Inventors: Meng-Shin Yen, Taipei (TW); William Wang, Taoyuan (TW); Chung-Cheng Chou, Luzhu Township, Taoyuan County (TW)

(73) Assignee: Crystalvue Medical Corporation, Taoyuan (TW)

( * ) Notice: Subject to any disclaimer, the term of this patent is extended or adjusted under 35 U.S.C. 154(b) by 375 days.

(21) Appl. No.: 13/294,657

(22) Filed: Nov. 11, 2011

(65) Prior Publication Data
US 2012/0120406 A1 May 17, 2012

(30) Foreign Application Priority Data
Nov. 12, 2010 (TW) ................. 99139084 A

(51) Int. Cl.
*G01B 9/02* (2006.01)
*A61B 5/00* (2006.01)
*A61B 3/10* (2006.01)

(52) U.S. Cl.
CPC .............. *A61B 5/0066* (2013.01); *A61B 3/102* (2013.01)

(58) Field of Classification Search
CPC ............. G01B 9/02049; G01B 9/0205; G01B 9/02091; G01N 21/4795
USPC .................................. 356/479, 497
See application file for complete search history.

(56) References Cited

U.S. PATENT DOCUMENTS

2003/0004412 A1* 1/2003 Izatt et al. ............... 600/425
2006/0066865 A1* 3/2006 Tsujita ..................... 356/479
2010/0290059 A1* 11/2010 Inoue ...................... 356/477

\* cited by examiner

*Primary Examiner* — Jonathan Hansen
(74) *Attorney, Agent, or Firm* — Patterson & Sheridan, LLP

(57) ABSTRACT

An optical apparatus is disclosed. The optical apparatus includes an optical scanning module and a rotation axis module. The optical scanning module is used to provide an optical signal for optical tomography. The rotation axis module and the optical scanning module are integrated. When the rotation axis module rotates, the rotation axis module makes the optical scanning module to perform a rotation scanning process to an object.

8 Claims, 5 Drawing Sheets

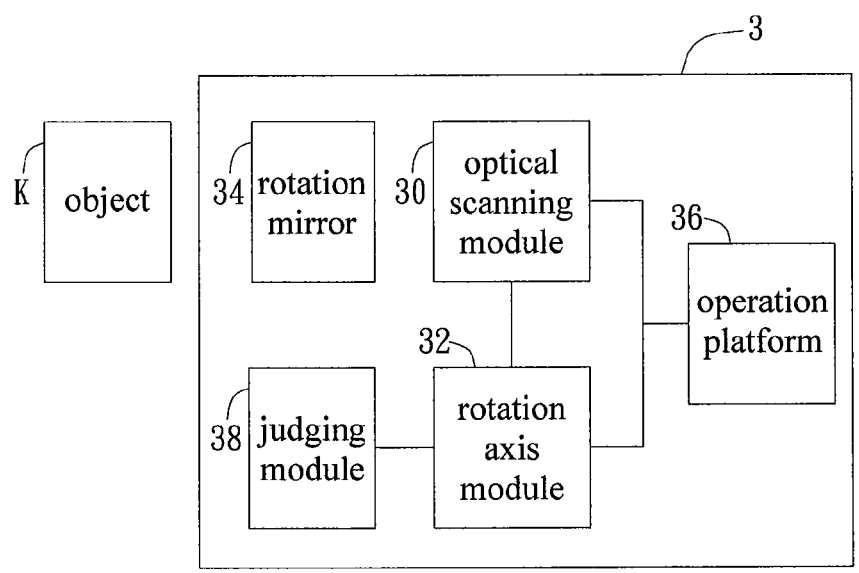
FIG. 3
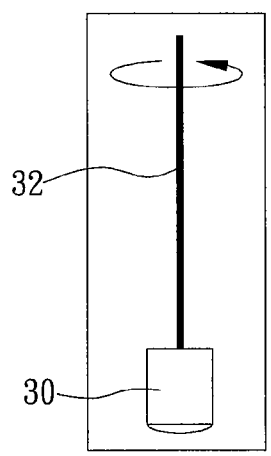      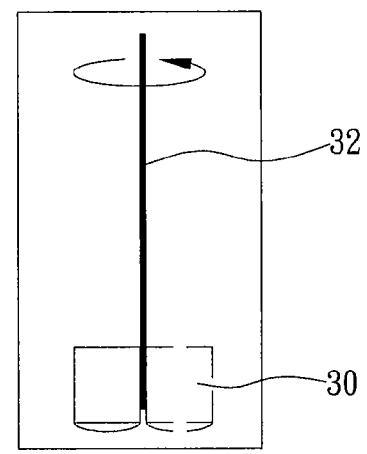
FIG. 4A                    FIG. 4B

OPTICAL APPARATUS AND OPERATING METHOD THEREOF

BACKGROUND OF THE INVENTION

1. Field of the Invention

The invention relates to optical detection, in particular, to an optical apparatus and operating method thereof capable of effectively enhancing the overall optical scanning detection efficiency through the disposition of the rotation axis.

2. Description of the Prior Art

In recent years, with the continuous development of the optical detection technology, several kinds of optical detection equipments have been developed. For example, the optical coherence tomography can be used as a fundus optical image apparatus to provide a cross-sectional image of the retina, and the optical coherence tomography uses the rotation of the rotation mirror to reflect the detected light to different directions to detect different locations of the fundus.

As shown in FIG. 1, because the size of the eye is relatively small and the fundus region R of the retina can be regarded similar to the circumference, the scanned region of the incident lines L1~L3 provided by the above-mentioned rotation mirror can be maintained in a certain focusing detection range, it is convenient for the user to use. However, once the design of the rotation mirror is used to detect the non-circumference large-area region S (e.g., the skin), because of the limitation of the rotation angle of the rotation mirror, the scanned region of the incident lines L1~L3 provided by the rotation mirror may fail to cover all regions to be detected on the large-area region S, some regions to be detected will not be detected.

As shown in FIG. 2, in order to improve the above-mentioned drawbacks, currently the entire non-circumference large-area region will be divided into several small regions M1~M6, and then each of the small regions M1~M6 will be scanned in order. However, each of the small regions M1~M6 will be limited by the rotation angle of the rotation mirror RM, therefore, it takes longer time to finish the scanning of the entire non-circumference large-area region, and the overall optical scanning detection efficiency will be seriously affected.

Therefore, the invention provides an optical apparatus and operating method thereof to solve the above-mentioned problems.

SUMMARY OF THE INVENTION

A first embodiment of the invention is an optical apparatus. In this embodiment, the optical apparatus includes an optical scanning module and a rotation axis module. The optical scanning module is used for providing an optical signal for optical tomography. The rotation axis module is integrated with the optical scanning module. When the rotation axis module rotates, the rotation axis module makes the optical scanning module to perform a rotation scanning process on an object.

In practical applications, the optical apparatus can further include a rotation mirror. The rotation mirror is disposed between the optical scanning module and the object. In the rotation scanning process, the rotation mirror will move in a 1-D direction relative to the object and cooperate with the rotation axis module to bring the rotation of the optical scanning module to perform a 2-D scan on the object. The rotation axis module and the optical scanning module form a concentrically designed set or an eccentrically designed set.

In addition, the optical apparatus can further include an operation platform used for integrating the optical scanning module and the rotation axis module, so that the rotation axis module can bring the optical scanning module to perform the rotation scanning process in three axes respectively. The operation platform can include a control module used for a user to control the operation platform. The control module is selected from a group formed by a joystick, a mouse, and a keyboard. The optical apparatus can further include a judging module used for judging whether the object and a detected region and a positioning point on the object are correct. If the judgment of the judging module is yes, the rotation axis module will bring the optical scanning module to perform the rotation scanning process.

A second embodiment of the invention is an optical apparatus operating method. In this embodiment, the optical apparatus includes an optical scanning module and a rotation axis module, the rotation axis module is integrated with the optical scanning module. The method includes the following steps: firstly, judging whether the object and a detected region and a positioning point on the object are correct; if the judgment is yes, when the rotation axis module rotates, the rotation axis module will bring the optical scanning module to perform a rotation scanning process on an object; afterward, the optical scanning module provides an optical signal for optical tomography.

Compared to the prior arts, the optical apparatus and operating method thereof in the invention will perform the rotation scanning through the integration of the rotation axis and the optical probe; therefore, the scanned area can be largely increased to enhance the overall scanning efficiency. And, 2-D area detection can be provided by 1-D direction scanning of the rotation mirror of the optical apparatus cooperating with the rotation of the rotation axis. Furthermore, the optical apparatus of the invention can include a platform of 6-degrees of freedom, and the platform can cooperate with a control apparatus similar to a joystick (or a mouse, a keyboard), a display, a micro-camera, and a sensor to perform the observation, positioning, and detection of the body parts of the patient, therefore, the human burden can be effectively reduced.

The advantage and spirit of the invention may be understood by the following detailed descriptions together with the appended drawings.

BRIEF DESCRIPTION OF THE APPENDED DRAWINGS

FIG. 3 illustrates a functional block diagram of the optical apparatus in the first embodiment of the invention.

FIG. 4A illustrates a schematic figure of the rotation axis module and the optical scanning module forming a concentrically designed set.

FIG. 4B illustrates a schematic figure of the rotation axis module and the optical scanning module forming an eccentrically designed set.

DETAILED DESCRIPTION OF THE INVENTION

Figure 1:
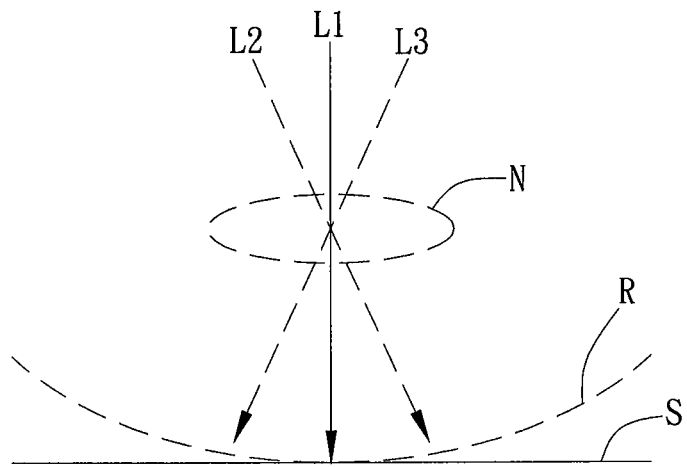
FIG. 1 illustrates a schematic figure of the focusing detection range of the rotation mirror in the prior art failing to cover all regions to be detected.
Figure 2:
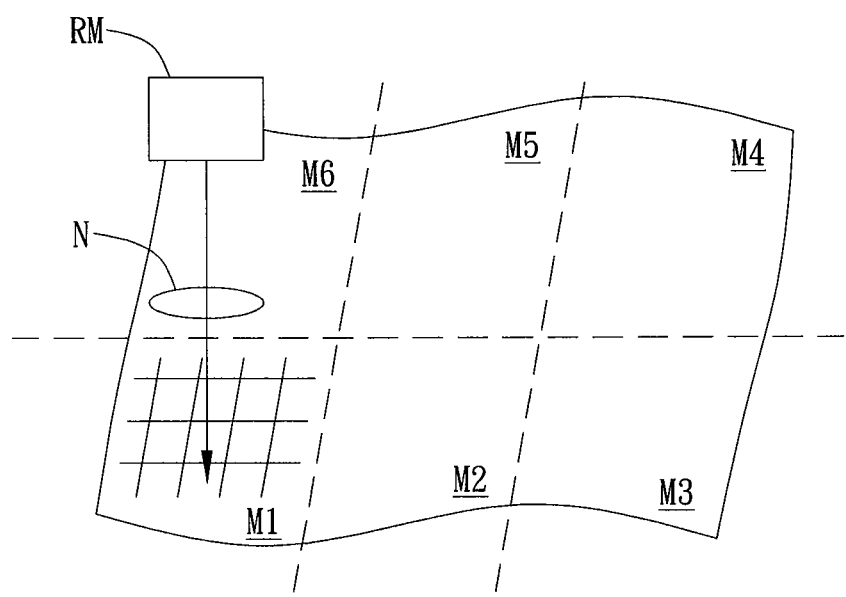
FIG. 2 illustrates a schematic figure of dividing the entire non-circumference large-area region into several small regions and scanning each of the small regions in order.

A first embodiment of the invention is an optical apparatus. hi this embodiment, the optical apparatus can be a skin optical image detection apparatus used to detect the non-circumference large-area region similar to the skin, but not limited to this case. In fact, the optical apparatus can be the optical coherence tomography or other similar equipments without specific limitations.

Please refer to FIG. 3. FIG. 3 illustrates the functional block diagram of the optical apparatus in this embodiment. As shown in FIG. 3, the optical apparatus 3 is used to perform an optical coherence tomography detection process on an object K. The optical apparatus 3 includes an optical scanning module 30, a rotation axis module 32, a rotation mirror 34, an operation platform 36, and a judging module 38. Wherein, the rotation mirror 34 is disposed between the optical scanning module 30 and the object K; the judging module 38 is coupled to the rotation axis module 32; the optical scanning module 30 is integrated with the rotation axis module 32, for example, the concentrically designed set shown in FIG. 4A or the eccentrically designed set shown in FIG. 4B.

In this embodiment, the judging module 38 is used to judge whether the object and a detected region and a positioning point on the object are correct. In fact, the judging module 38 has the image capturing function and the image comparing function, therefore, the judging module 38 can judge whether the object and the detected region and the positioning point on the object are correct by comparing the images of the object and the detected region and the positioning point on the object with the reference images obtained in previous optical detection. If the judgment of the judging module 38 is yes, the rotation axis module 32 will bring the optical scanning module 30 to perform the rotation scanning process.

The optical scanning module 30 is used for providing an optical signal for optical tomography. When the rotation axis module 32 rotates, the rotation axis module 32 brings the optical scanning module 30 to perform the rotation scanning process on the object K. In the rotation scanning process, the rotation mirror 34 moves in a 1-D direction relative to the object K and cooperates with the rotation axis module 32 to bring the rotation of the optical scanning module 30 to perform a 2-D scan on the object K.

In order to improve the drawback that the scanning rate of the optical apparatus is slower in the prior arts, the optical scanning module 30 of the optical apparatus 3 in the invention is integrated with the rotation axis module 32. In fact, the optical scanning module 30 can be an optical probe, but not limited to this case.

Figure 5A:
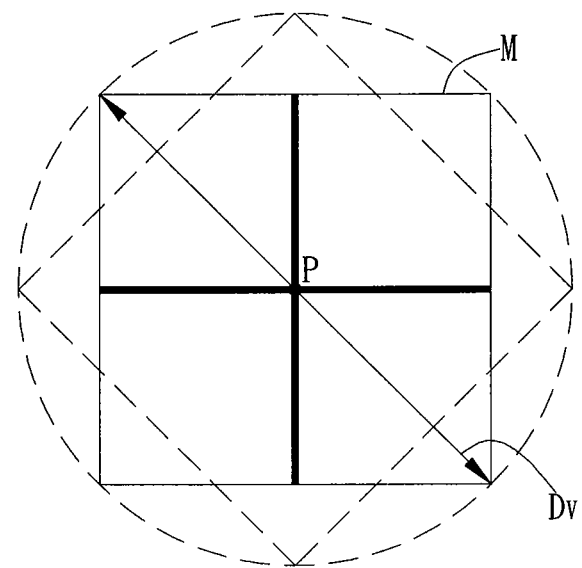
FIG. 5A illustrates a schematic figure of the maximum scanning range of the optical probe under the fixed position in the prior art.

Please refer to FIG. 5A. FIG. 5A illustrates a schematic figure of the maximum scanning range of the optical probe under the fixed position in the prior art. As shown in FIG. 5A, if a single optical probe P under the fixed position can provide the effective detection diameter Dv through the rotation mirror M, under the above-mentioned conditions, the maximum scanning range of the optical probe P under the fixed position is $(0.707Dv)^2$ in the prior art.

Figure 5B:
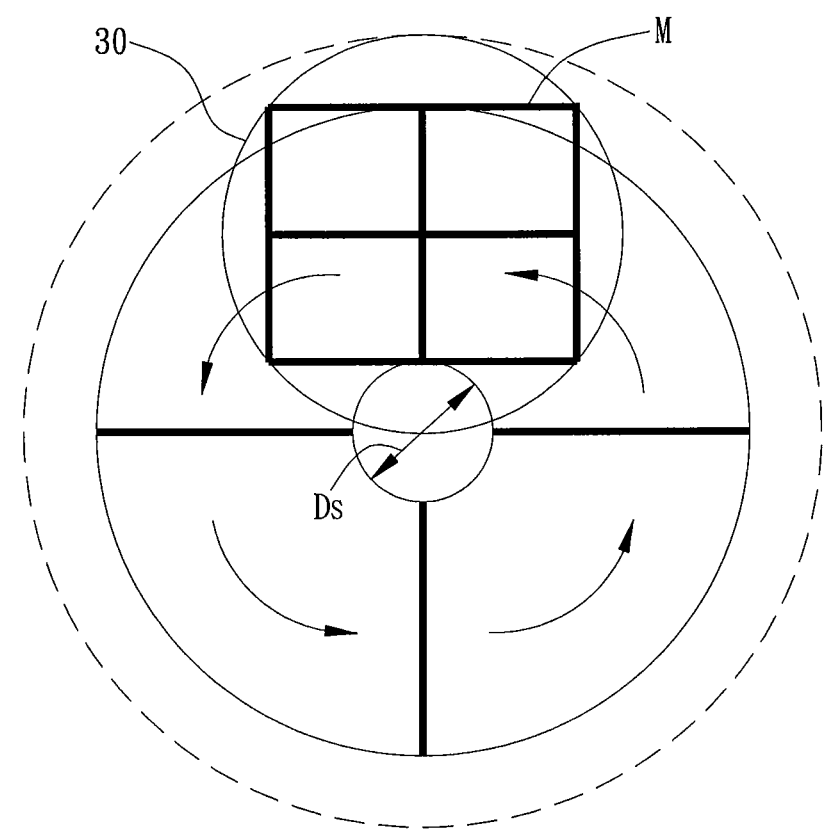
FIG. 5B illustrates a schematic figure of the maximum scanning range of the integrated optical probe and rotation axis module in the invention.

On the other hand, please refer to FIG. 5B. FIG. 5B illustrates a schematic figure of the maximum scanning range of the integrated optical scanning module (optical probe) 30 and rotation axis module 32 in the invention. If the diameter of the rotation axis in the rotation axis module 32 is Ds, the maximum scanning range the integrated optical scanning module (optical probe) 30 and rotation axis module 32 will become $[(0.5Ds+1.207Dv)^2-(0.5Ds)^2]$. If Ds is 0, the maximum scanning range shown in FIG. 5B will be 2.9 times larger than the maximum scanning range shown in FIG. 5A. Therefore, after the optical probe 30 of the optical apparatus 3 in the invention is integrated with the rotation axis of the rotation axis module 32, the maximum scanning range can be effectively increased and the overall scanning rate can be also enhanced.

It should be noticed that the optical scanning module (optical probe) 30 is integrated with the rotation axis, therefore, when the light path of the optical probe is designed, the complication of designing the rotation mirror can be reduced. For example, as shown in FIG. 5B, in the rotation scanning process, the rotation mirror 34 only moves in the 1-D direction relative to the object K and cooperates with the rotation axis module 32 to bring the rotation of the optical scanning module (optical probe) 30 to perform the 2-D scan on the object K. In practical applications, the integration of the optical probe 30 and the rotation axis module 32 can effectively increase the maximum scanning range of the optical apparatus 3 at least two times, but not limited to this case.

Figure 6:
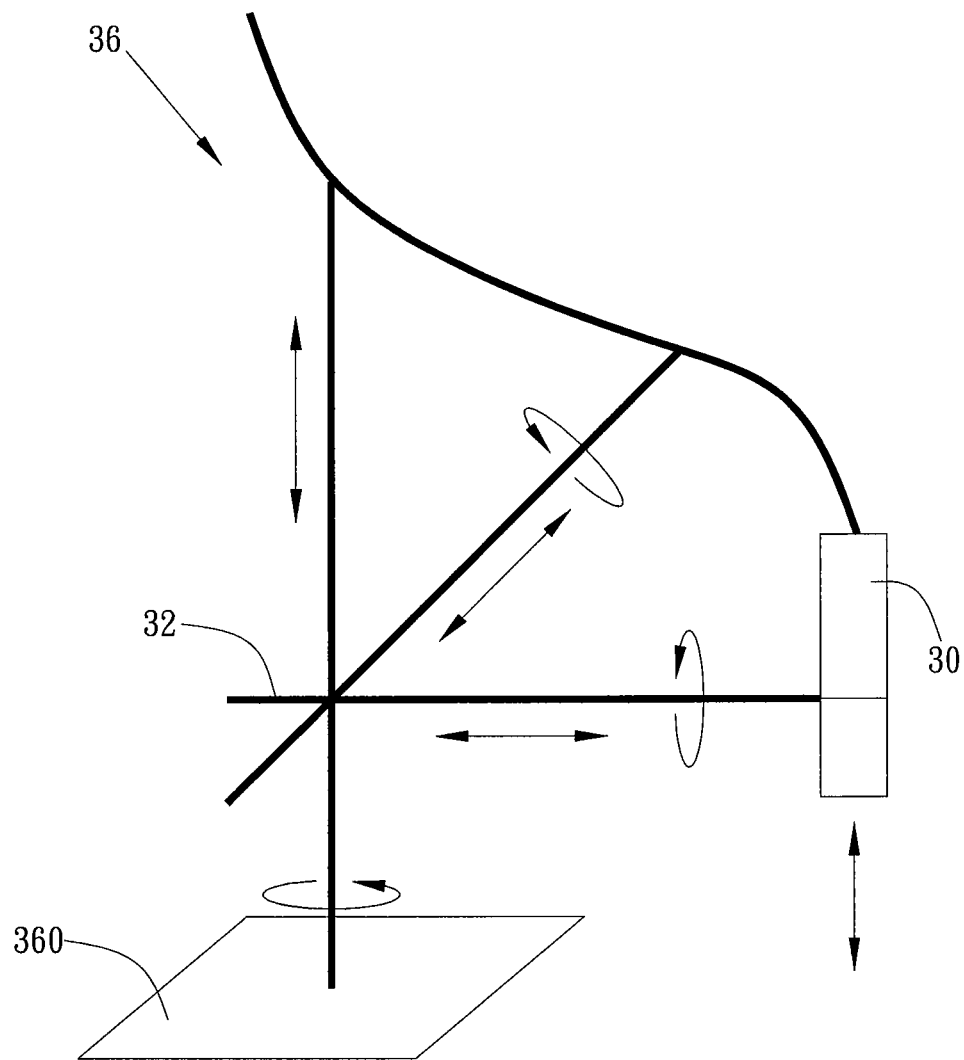
FIG. 6 illustrates a schematic figure of the operation platform of the optical apparatus.

Please refer to FIG. 6. FIG. 6 illustrates a schematic figure of the operation platform 36 of the optical apparatus 3. As shown in FIG. 6, the operation platform 36 can be a platform of 6-degrees of freedom used to integrate the optical scanning module 30 and the rotation axis module 32, so that the rotation axis module 32 can bring the optical scanning module 30 to perform the rotation scanning process on the three axes: X-axis, Y-axis, and Z-axis. In addition, the operation platform 36 can also include a control module 360 for the user to control the operation platform 36. In fact, the control module 360 can be a joystick, a mouse, a keyboard, or other similar apparatus, but not limited to this case.

Figure 7:
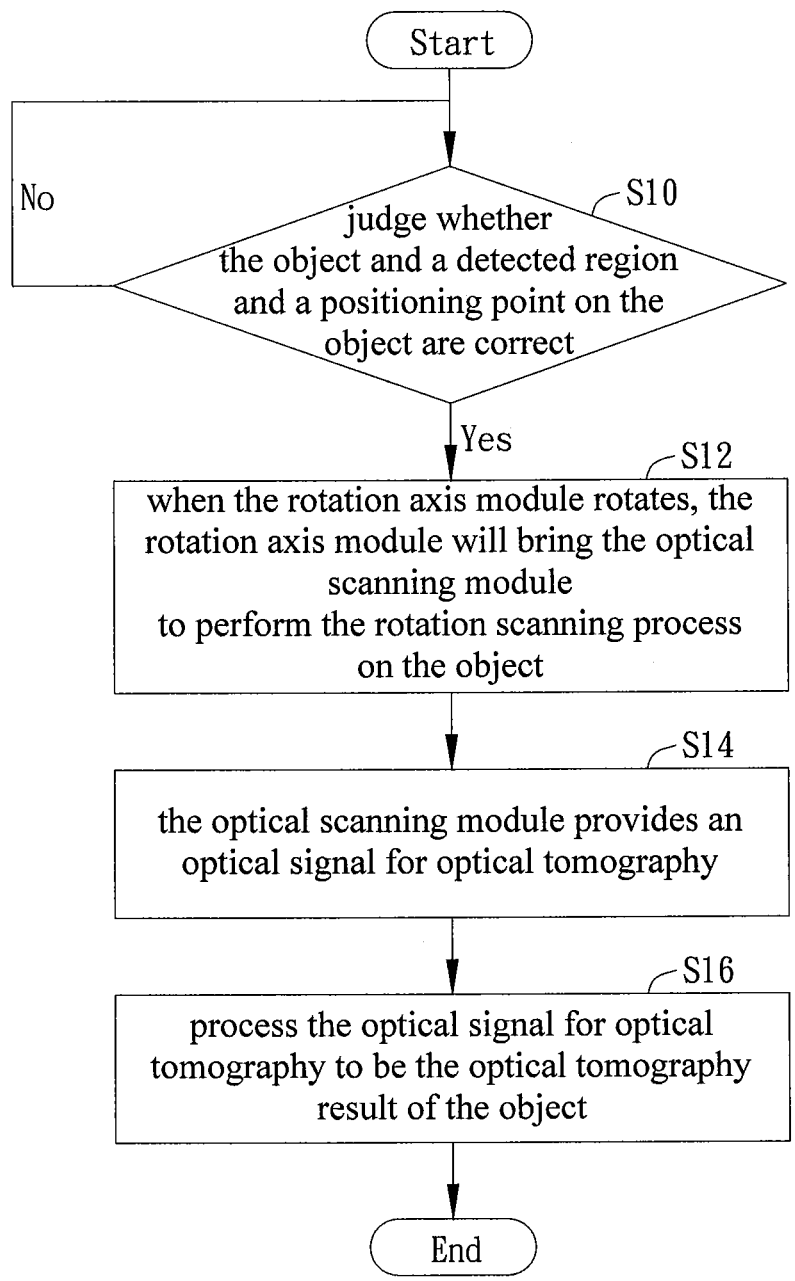
FIG. 7 illustrates a flowchart of the optical apparatus operating method in the second embodiment of the invention.

A second embodiment of the invention is an optical apparatus operating method. In this embodiment, the optical apparatus includes an optical scanning module and a rotation axis module, and the rotation axis module is integrated with the optical scanning module. Please refer to FIG. 7. FIG. 7 illustrates a flowchart of the optical apparatus operating method in this embodiment.

As shown in FIG. 7, at first, the method performs the step S10 to judge whether the object and a detected region and a positioning point on the object are correct. In fact, the detected region on the object can be a non-circumference large-area region similar to the skin, but not limited to this case.

If the judgment of the step S10 is YES, the method will perform the step S12, when the rotation axis module rotates, the rotation axis module will bring the optical scanning module to perform the rotation scanning process on the object. In fact, the rotation axis module can bring the optical scanning module to perform the rotation scanning process on the three axes: X-axis, Y-axis, and Z-axis respectively, but not limited to this case. If the judgment of the step S10 is NO, the method will perform the step S10 again.

Then, the method performs the step S14, the optical scanning module provides an optical signal for optical tomography. At last, the method performs the step S16 to process the optical signal for optical tomography to be the optical tomography result of the object.

In practical applications, the optical apparatus can further include a rotation mirror. The rotation mirror is disposed between the optical scanning module and the object. In the rotation scanning process, the rotation mirror will move in a 1-D direction relative to the object and cooperate with the rotation axis module to bring the rotation of the optical scanning module to perform a 2-D scan on the object.

Compared to the prior arts, the optical apparatus and operating method thereof in the invention will perform the rotation scanning through the integration of the rotation axis and the optical probe; therefore, the scanned area can be largely increased to enhance the overall scanning efficiency. And, 2-D area detection can be provided by 1-D direction scanning of the rotation mirror of the optical apparatus cooperating with the rotation of the rotation axis. Furthermore, the optical apparatus of the invention can include a platform of 6-degrees of freedom, and the platform can cooperate with a control apparatus similar to a joystick (or a mouse, a keyboard), a display, a micro-camera, and a sensor to perform the observation, positioning, and detection of the body parts of the patient, therefore, the human burden can be effectively reduced.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical apparatus, comprising:
   an optical scanning module, for providing an optical signal toward an object for optical tomography;
   a rotation axis module, disposed out of the optical scanning module, when the rotation axis module rotates, the rotation axis module making the optical scanning module to perform a rotation scanning process on the object; and
   a rotation mirror, disposed between the optical scanning module and the object instead of being integrated with the optical scanning module, in the rotation scanning process, the rotation mirror moving in a 1-D direction relative to the object and cooperating with the rotation axis module to bring the rotation of the optical scanning module to perform a 2-D scan on the object;
   wherein an end of the rotation axis module is coupled to a center of a bottom outer surface of the optical scanning module or coupled to a side outer surface of the optical scanning module to bring the optical scanning module to rotate through the bottom outer surface or the side outer surface of the optical scanning module, and the optical signal provided by the optical scanning module is not emitted toward the rotation axis module; the optical scanning module is an optical probe, and the optical probe is integrated with the rotation axis module to increase a maximum scanning range and a scanning rate of the optical apparatus.

2. The optical apparatus of claim 1, wherein the rotation axis module and the optical scanning module form a concentrically designed set or an eccentrically designed set.

3. The optical apparatus of claim 1, further comprising:
   an operation platform, for integrating the optical scanning module and the rotation axis module, so that the rotation axis module can bring the optical scanning module to perform the rotation scanning process in three axes respectively.

4. The optical apparatus of claim 3, wherein the operation platform includes a control module used for a user to control the operation platform, the control module is selected from a group formed by a joystick, a mouse, and a keyboard.

5. The optical apparatus of claim 1, further comprising:
   a judging module, coupled to the rotation axis module, for judging whether the object and a detected region and a positioning point on the object are correct, when the judgment of the judging module is yes, the rotation axis module bringing the optical scanning module to perform the rotation scanning process.

6. A method of operating an optical apparatus, the optical apparatus comprising an optical scanning module and a rotation axis module, the rotation axis module being disposed out of the optical scanning module, the method comprising steps of:
   (a) when the rotation axis module rotates, the rotation axis module bringing the optical scanning module to perform a rotation scanning process on an object; and
   (b) the optical scanning module providing an optical signal toward the object for optical tomography;
   wherein an end of the rotation axis module is coupled to a center of a bottom outer surface of the optical scanning module or coupled to a side outer surface of the optical scanning module to bring the optical scanning module to rotate through the bottom outer surface or the side outer surface of the optical scanning module, and the optical signal provided by the optical scanning module is not emitted toward the rotation axis module; the optical scanning module is an optical probe, and the optical probe is integrated with the rotation axis module to increase a maximum scanning range and a scanning rate of the optical apparatus, the optical apparatus further comprises a rotation mirror disposed between the optical scanning module and the object instead of being integrated with the optical scanning module, in the rotation scanning process, the rotation mirror moves in a 1-D direction relative to the object and cooperates with the rotation axis module to perform a 2-D scan on the object.

7. The method of claim 6, wherein the rotation axis module brings the optical scanning module to perform the rotation scanning process in three axes respectively.

8. The method of claim 6, further comprising steps of:
   (c) judging whether the object and a detected region and a positioning point on the object are correct; and
   when the judgment of the step (c) is yes, the method performing the step (a).

* * * * *